United States Patent [19]

Daluge et al.

[11] 4,438,267

[45] Mar. 20, 1984

[54] MONOHETERORING COMPOUNDS AND THEIR USE

[76] Inventors: Susan M. Daluge, 297 Azalea Dr., Chapel Hill, N.C. 27514; Paul M. Skonezny, 1513 Cotherstone Dr., Durham, N.C. 27712

[21] Appl. No.: 319,644

[22] Filed: Nov. 9, 1981

[30] Foreign Application Priority Data

Nov. 11, 1980 [GB] United Kingdom ................ 8036135

[51] Int. Cl.$^3$ .................. C07D 239/47; C07D 239/49
[52] U.S. Cl. .................................... 544/309; 544/313; 544/315; 544/317; 544/318; 544/325; 544/330; 544/332; 544/334; 424/251
[58] Field of Search ............... 544/325, 334, 309, 313, 544/315, 317, 318, 330, 332

[56] References Cited

U.S. PATENT DOCUMENTS 4,039,543  8/1977  Kompis ................................ 544/334

FOREIGN PATENT DOCUMENTS 957797   7/1960  United Kingdom ................ 544/325
1468374  3/1977  United Kingdom ................ 544/325

OTHER PUBLICATIONS

Wamhoff, Chem. Ber. 100, 1324, (1967).
Yoshimoto, J. Med. Chem. 19 71, (1976).

*Primary Examiner*—Robert Gerstl
*Attorney, Agent, or Firm*—Donald Brown

[57] ABSTRACT

Novel 2,4-diamino-5-(substituted naphthylmethyl)-pyrimidines have been found to have superior antibacterial activity.

1 Claim, No Drawings

MONOHETERORING COMPOUNDS AND THEIR USE

The present invention relates to novel 2,4-diamino-5-(substituted)pyrimidines, to pharmaceutical compositions containing them, to processes for preparing them and their compositions, to intermediates for making them and to their use in the treatment of microbial infections.

Certain 2,4-diamino-5-benzylpyrimidines have been demonstrated to be potent inhibitors of dihydrofolate reductase (DHFR) which catalyses the reduction of dihydrofolic acid to tetrahydrofolic acid (THFA). This property has been shown frequently to result in useful pharmaceutical properties particularly in the treatment of bacterial infections. Thus, U.K. Patent Specification No. 875,562 discloses inter alia compounds of the formula (I):

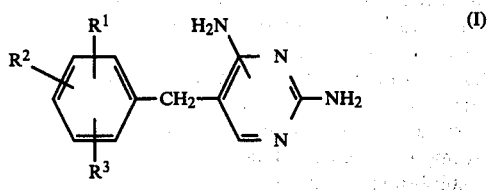

wherein $R^1$, $R^2$ and $R^3$ are the same or different $C_{1-4}$ alkoxy groups. Trimethoprim, 2,4-diamino-5-(3,4,5-trimethoxybenzyl)pyrimidine, is specifically disclosed in U.K. Pat. No. 875,562 and is the most active general antibacterial agent amongst the 2,4-diamino-5-benzylpyrimidines known to date. Due to their mode of action, these benzylpyrimidines potentiate the antibacterial activity of the sulphonamides and trimethoprim has been used extensively over the last decade in human therapy in combination with various sulphonamides, and in particular with sulphamethoxazole, for the treatment of bacterial infections.

U.K. Patent Specification No. 957797 discloses inter alia 2,4-diamino-5-(1-naphthylmethyl)pyrimidine which is described as having useful biological activity. Further investigation revealed that this compound was considerably inferior to trimethoprim.

Unfortunately, whilst trimethoprim has an excellent level of activity against most aerobic bacteria its activity against anaerobic bacteria is less impressive and its activity against certain aerobic bacteria could beneficially be improved upon. A novel group of 2,4-diamino-5-substituted pyrimidines has now been found many of the compounds having a general level of activity against aerobic bacteria comparable to that of trimethoprim whilst having a superior level of activity against anaerobic bacteria. Some of these compounds are also considerably superior to trimethoprim against gram positive aerobic bacteria, particularly *Staphylococcus aureus* and some compounds have a different pharmacokinetic profile, for example, a longer half life, than trimethoprim.

Accordingly, the present invention provides a compound of the formula (II):

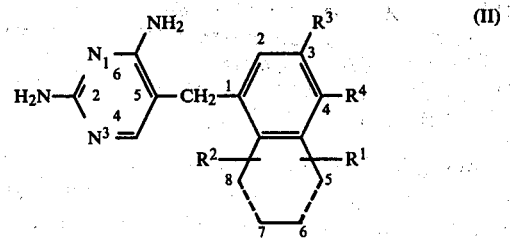

or a salt, N-oxide or acyl derivative thereof, wherein the dotted line represent single or double bonds, $R^1$ and $R^2$ are the same or different and each is hydrogen, halogen, $C_{1-4}$ alkyl, $C_{1-4}$ alkylthio or $C_{1-4}$ alkoxy, optionally substituted by halogen, hydroxy or $C_{1-2}$ alkoxy or $R^1$ and $R^2$ are linked to the same carbon atom to form a group C=O,

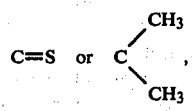

$R^3$ and $R^4$ are the same or different and each is hydrogen, halogen, $C_{2-4}$ alkenyl, $C_{2-4}$ alkenyloxy, nitro, cyano, hydroxy, mercapto, a group $-OSO_2R^7$ or $-S(O)_nR^7$ wherein $R^7$ is $C_{1-3}$ alkyl and n is 0, 1 or 2, a group $-COR^8$ wherein $R^8$ is methyl, ethyl, methoxy, ethoxy, amino, methylamino, ethylamino, dimethylamino, or diethylamino, or each is amino optionally substituted by one or more $C_{1-4}$ alkyl or $C_{1-4}$ acyl or the nitrogen atom forms part of a five or six membered heterocyclic ring, $C_{1-4}$ alkyl or $C_{1-4}$ alkoxy each optionally substituted by halogen, hydroxy, or $C_{1-2}$ alkoxy, or $R^3$ and $R^4$ together form a methylenedioxy group; except that when $R^1$, $R^2$ and $R^3$ are all hydrogen $R^4$ is neither hydroxy nor hydrogen and $R^1$ and $R^2$ are not substituents other than hydrogen on the carbon atom at the 8-position.

It will be readily apparent that $R^1$ will not be =O, =S, or gem dimethyl when the compound of the formula (II) is a substituted 2,4-diamino-5-naphthylmethyl-pyrimidine.

Particularly suitable compounds of the formula (II) include those of the formula (III):

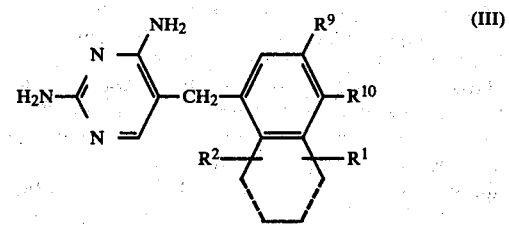

or a salt, N-oxide or acyl derivative thereof wherein the dotted lines, $R^1$ and $R^2$ are as hereinbefore defined and $R^9$ and $R^{10}$ are the same or different and each is hydrogen, halogen, $C_{2-4}$ alkenyl, $C_{2-3}$ alkenyloxy, nitro, a group $NR^{11}R^{12}$ wherein $R^{11}$ and $R^{12}$ are the same or different and each is hydrogen, methyl or ethyl or $NR^{11}R^{12}$ forms a five or six-membered heterocyclic ring, cyano, hydroxy, a group $-S(O)_nR^7$ or $COR^8$ as hereinbefore defined, or $C_{1-4}$ alkyl or $C_{1-4}$ alkoxy each optionally substituted by halogen, hydroxy or $C_{1-3}$ alkoxy, except that $R^9$ and $R^{10}$ are not both hydrogen or halogen, that either $R^1$ and $R^2$ are not substituents on the carbon atom at the 8-position.

Suitably $R^9$ is $C_{2-3}$ alkenyl, halogen, a group $S(O)_nR^7$ as hereinbefore defined, cyano, amino, mono-$C_{1-3}$-alkyl substituted amino, or $C_{1-3}$ alkyl or $C_{1-3}$ alkoxy each optionally substituted by halogen, hydroxy or $C_{1-3}$ alkoxy.

Most suitably $R^9$ is methoxy, ethoxy, methoxyethoxy, methyl, ethyl, propyl, vinyl, allyl, propenyl, halogen, methylthio, ethylthio. Preferably $R^9$ is methyl, methoxy or ethoxy, particularly methoxy.

Suitably $R^{10}$ is hydrogen, hydroxy, amino, mono- or di-$C_{1-3}$ alkyl substituted amino, nitro, cyano, pyrrolyl, a group —$S(O)_nR^7$ or —$COR^8$ as hereinbefore defined or $R^{10}$ is $C_{1-3}$ alkoxy optionally substituted by halogen, hydroxy or $C_{1-3}$ alkoxy.

Most suitably $R^{10}$ is hydrogen, hydroxy, methoxy, ethoxy, nitro, amino, methylamino, dimethylamino, ethylamino, diethylamino, methylthio, ethylthio or pyrrolyl. Preferably $R^{10}$ is methoxy, amino, mono- or di-methylamino or methylthio, particularly methoxy, dimethylamino or methylthio.

Preferably the dotted lines represent double bonds.

Suitably $R^1$ is hydrogen, gem dimethyl, $C_{1-3}$ alkyl optionally substituted by halogen, $C_{1-3}$-alkylthio or $C_{1-3}$ alkoxy optionally substituted by halogen, hydroxy or $C_{1-2}$ alkoxy. Most suitably $R^1$ is hydrogen, methyl, trifluoromethyl or methoxy and preferably $R^1$ is hydrogen.

Suitably $R^2$ is hydrogen, $C_{1-3}$ alkyl, optionally substituted by halogen, $C_{1-3}$-alkylthio or $C_{1-3}$ alkoxy optionally substituted by halogen, hydroxy or $C_{1-2}$ alkoxy. Most suitably $R^2$ is hydrogen, methyl, trifluoromethyl or methoxy and preferably $R^2$ is hydrogen.

One group of preferred compounds of the present invention includes those of the formula (IV):

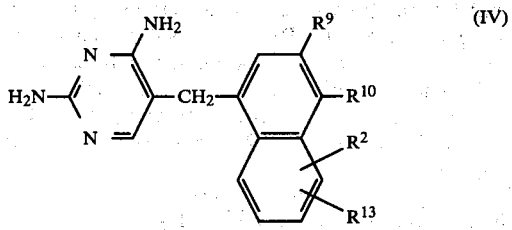

or a salt, N-oxide or acyl derivative thereof, wherein $R^2$, $R^9$ and $R^{10}$ are as hereinbefore defined and $R^{13}$ is hydrogen, halogen, $C_{1-3}$ alkylthio $C_{1-3}$ alkyl or $C_{1-3}$ alkoxy optionally substituted by halogen, hydroxy or $C_{1-2}$ alkoxy, except that when $R^2$, $R^9$ and $R^{13}$ are all hydrogen, $R^{10}$ is neither hydrogen nor hydroxy. Suitably $R^9$ is hydrogen, methoxy, ethoxy, mono-$C_{1-3}$-alkylamino, $C_{2-3}$ alkenyl, $C_{1-3}$ alkyl or methylthio. Most suitably $R^9$ is hydrogen, methoxy, ethoxy, or methylthio. Preferably $R^9$ is hydrogen, methoxy or ethoxy.

Suitably $R^{10}$ is hydrogen, methoxy, ethoxy, methylthio, or a group $NR^{13}R^{14}$ as hereinbefore defined. Most suitably $R^{10}$ is methoxy, ethoxy, amino or dimethylamino. Preferably $R^{10}$ is methoxy, ethoxy or amino.

Suitably $R^2$ is hydrogen, alkylthio, methoxy, ethoxy or methoxyethoxy. Preferably $R^2$ is hydrogen or methoxy.

Suitably $R^{13}$ is hydrogen, methylthio or methoxy and preferably $R^{13}$ is hydrogen or methoxy.

Preferred compounds of the present invention include:

2,4-diamino-5-(4-methoxy-1-naphthylmethyl)pyrimidine,
2,4-diamino-5-(4-amino-3-methoxy-1-naphthylmethyl)pyrimidine,
2,4-diamino-5-(4-hydroxy-3-methoxy-1-naphthylmethyl)pyrimidine,
2,4-diamino-5-(3,4-dimethoxy-1-naphthylmethyl)pyrimidine,
2,4-diamino-5-(4-amino-3,6-dimethoxy-1-naphthylmethyl)pyrimidine, or a salt, N-oxide or acyl derivative thereof.

Suitably the compounds of the formula (II) to (IV) are present in the form of the free base or an acid addition salt thereof.

Certain compounds of the formula (II) whilst having some antibacterial activity in their own right are also useful as intermediates in the preparation of other compounds of the formula (II) having interesting antibacterial activity.

The compounds of the formula (II) are bases and, as such, form acid addition salts with acids. Suitable acid addition salts of the compounds of the formula (II) include those formed with both organic and inorganic acids. Such acid addition salts will normally be pharmaceutically acceptable. Thus, preferred salts include those formed from hydrochloric, sulphuric, citric, tartaric, phosphoric, lactic, benzoic, glutamic, aspartic, pyruvic, acetic, succinic, fumaric, maleic, oxaloacetic, isethionic, stearic, fumaric, methanesulphonic, toluene p-sulphonic, lactobionic and glucuronic acids.

When the compounds of the formulas (II) to (IV) are substituted by hydroxy groups, alkali metal salts of these compounds may be formed and these salts also comprise part of the present invention. Particularly suitable alkali metal salts are those formed with sodium and potassium.

Suitable acyl derivatives are those wherein an amino group is substituted by a group —$COR^{14}$ wherein $R^{14}$ is hydrogen or $C_{1-11}$ alkyl or $C_{2-11}$ alkenyl, preferably $C_{1-4}$ alkyl or $C_{2-4}$ alkenyl, optionally substituted by carboxy, carb-$C_{1-4}$ alkoxy, nitrile, amino, chlorine or phenoxy optionally substituted by halogen, methyl or methoxy, the alkyl or alkenyl groups being optionally interspersed with one or more oxygen atoms or forming part or the whole of a cycloaliphatic ring or $R^{14}$ may represent a $C_{6-10}$ aromatic or $C_{6-10}$ araliphatic residue optionally substituted by one or more chlorine atoms or methyl, $OCH_2COOH$, carb-$C_{1-4}$ alkoxy or a heterocyclic group containing one or more nitrogen, oxygen or sulphur atoms. Preferred acyl derivatives are those wherein the amino group at the 2-position of the pyrimidine ring is substituted, particularly those wherein the amino group is substituted by acetyl or by an acyl group derived from an amino acid such as a glycyl group.

Suitable N-oxides of compounds of the formula (II) include those formed by oxidation of either or both of the nitrogen atoms in the pyrimidine ring.

The preparation of salts, acyl derivatives and N-oxides is carried out by conventional methods well known to those skilled in the art.

Pharmaceutically acceptable acid addition salts of compounds of the formula (II) form a particularly preferred aspect of the present invention.

In a further aspect, the present invention provides a pharmaceutical composition comprising a compound of the formula (II) in a combination with a pharmaceutically acceptable carrier. By the terms "pharmaceutical composition" and "pharmaceutically acceptable carrier" are meant those compositions and carriers suitable for use in human and/or veterinary medicine.

The compounds of the formula (II) can conveniently be presented in the compositions of the present invention in an effective unit dosage form, that is to say in an amount sufficient to be effective against the bacterial organism in vivo.

The pharmaceutically acceptable carriers present in the compositions of the present invention are materials recommended for the purpose of administering the medicament. These may be liquid, solid or gaseous materials, which are otherwise inert or medically acceptable and are compatible with the active ingredient.

These pharmaceutical compositions may be given parenterally, orally, used as a suppository, applied as an ophthalmic solution, or applied topically as an ointment, cream or powder. However, oral and parenteral administration of the compositions is preferred for human use. For veterinary use, intramammary as well as oral and parenteral administration is preferred.

For oral administration, fine powders or granules will contain diluting, dispersing and/or surface active agents, and may be presented in a draught, in water or in a syrup, in capsules or cachets in the dry state or in a non-aqueous suspension wherein suspending agents may be included, or in a suspension in water or syrup. Where desirable or necessary, flavouring, preserving, suspending, thickening or emulsifying agents can be included.

For parenteral administration, the compounds may be presented in sterile aqueous injection solutions which may contain antioxidants or buffers.

As stated above, free base or a salt thereof may be administered in its pure form unassociated with other additives in which case a capsule or cachet is the preferred carrier.

Other compounds which may be included are, for example, medically inert ingredients, e.g. solid and liquid diluents such as lactose, glucose, starch of calcium phosphate for tablets or capsules; olive oil or ethyl oleate for soft capsules; and water or vegetable oil for suspensions or emulsions; lubricating agents such as talc or magnesium stearate; gelling agents such as colloidal clays; thickening agents such as gum tragacanth or sodium alginate; and other therapeutically acceptable accessory ingredients such as humectants, preservatives, buffers, and antioxidants which are useful as carriers in such formulations.

Alternatively the active compound may be presented in a pure form as an effective unit dosage, for instance, compressed as a tablet or the like.

For veterinary use, different intramammary formulations will normally be prepared for use in dry cows and for use in milking cows. Thus, formulations for dry cow use will normally be in an oil, such as peanut oil, gelled with a gelling agent such as aluminium monostearate. Formulations for milking cow use will usually contain an emulsifying agent (for example Tween 20 or a polysorbate) and a milk miscible carrier such as peanut oil or a mineral oil.

It may be advantageous to include the compounds of formula (II) in a pharmaceutical composition which includes other active ingredients for example p-aminobenzoic acid competitors such as sulphonamides.

Of known p-aminobenzoic acid competitors, the following sulphonamide compounds (or pharmaceutically acceptable salts thereof) are particularly useful:

Sulfanilamide, Sulfadiazine, Sulfamethisazole, Sulfapyridine, Sulfathiazole, Sulfamerazine, Sulfamethazine, Sulfisoxazole, Sulformethoxine, 2-(p-Aminobenzene)-sulfonamide-3-methoxypyrazine (Kelfizina), Sulfonyldianiline, Mafenide, 5-Sulfanilamido-2,4-dimethyl pyrimidine, 4-($N^1$-Acetylsulfanilamido)-5,6-dimethoxy pyrimidine, 3-Sulfanilamido-4,5-dimethyl isoxazole, 4-Sulfanilamido-5-methoxy-6-decyloxy pyrimidine sulfamono-methoxine, 4-p-(8-Hydroxy quinolinyl-4-azo)-phenylsulfanilamido-5,6-dimethoxy pyrimidine, Sulfadimethoxine, Sulfadimidine, Sulfamethoxazole, Sulfamoxole, Sulfadoxine, Sulfaguanidine, Sulfathiodimethoxine, Sulfaquinoxaline, and p-(2-Methyl-8-hydroxyquinolinyl-5-azo)phenyl sulfanilamido-5,6-dimethoxy pyrimidine.

However, the most preferred combinations include those containing Sulfadizine, Sulfamethoxazole, Sulfadoxine, Sulfamoxole or Sulfadimidine. The ratio of the compound of the formula (II) to sulphonamide will normally be from 3:1 to 1:10, for example 1:1 to 1:5. A particularly preferred composition of the present invention comprises a compound of formula (II) and a sulphonamide in a ratio of 1:2 to 1:5 preferably together with a pharmaceutically acceptable carrier.

Tablets or other forms of presentation provided in discrete units may conveniently contain an amount of compound of the formula (II) which is effective at a dosage or as a multiple of the same, for instance for human use, units containing 2.5 to 200 mg usually around 30 to 100 mg, for veterinary use, units containing 30 to 500 mg.

The pharmaceutical compositions of the present invention can be prepared by the admixture of a compound of the formula (II) with a pharmaceutically acceptable carrier. Other active ingredients, such as a sulfonamide, or conventional pharmaceutical excipients may be admixed as required.

The compounds of the present invention are useful for the treatment of gram negative aerobic, gram positive aerobic or anaerobic bacterial infections in mammals. They are particularly useful in the treatment of Staphylococcal infections for example mastitis in cattle. Neisseria infections in humans, for example *N. gonorrhea*, acne in humans, and anaerobic infections. Most compounds also have an excellent level of general antibacterial activity.

Still another aspect of the present invention provides a method for the treatment or prophylaxis of bacterial infections in mammals by the administration of an effective non-toxic antibacterial amount of a compound of formula (II) or a pharmaceutically acceptable salt thereof, or a composition as hereinbefore described.

As indicated above, the compounds of the formula (II) are generally useful in treating bacterial infections by rectal, parenteral, topical or oral administration. The compounds of formula (II) are normally administered at a dose from 0.1 mg/kg to 30 mg/kg per day and preferably 1 mg/kg to 10 mg/kg. The dose range for adult humans is generally from 25 to 300 mg/kg and preferably 100 to 200 mg/day.

The dose range for intramammary administration of the compounds of the formula (II) is generally from 100 to 500 mg, preferably 200 mg to 400 mg, per quarter of the udder to dry cows. Milking cows will normally receive four to six medications of a composition of the present invention, a dose being conveniently administered at milking time (i.e. twice daily) to each of the desired quarters of the udder. Dry cows will normally receive only one medication of a composition of the present invention, one dose being provided to each of the four quarters of the udder.

The compounds of formula (II) and their pharmaceutically acceptable salts may be prepared by methods known for the synthesis of compounds of analogous structure.

Thus the present invention provides a process for preparation of compounds of the formula (II) as hereinbefore defined which process comprises:

(a) (i) the reaction of a guanidine salt with a compound of the formula (V) or (VI):

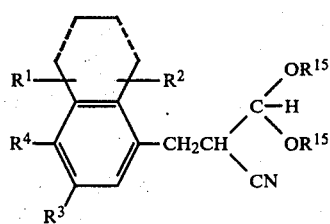

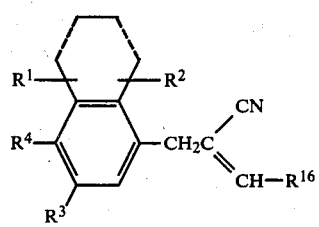

wherein $R^1$ to $R^4$ and the dotted lines are as hereinbefore defined, $R^{15}$ is a $C_{1-4}$ alkyl group and $R^{16}$ is a nucleophilic leaving group such as a $C_{1-4}$ alkoxy group or an amino, $C_{1-4}$ alkylamino, benzylamino, di-($C_{1-4}$)alkylamino, naphthylamino, optionally substituted anilino, morpholino, piperidino or N-methyl piperazino group and most preferably $R^{16}$ is an anilino group:

(ii) the reaction of a compound of the formula (VII):

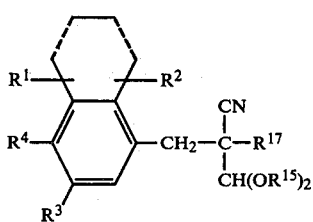

wherein $R^1$ to $R^4$, $R^{15}$ and the dotted lines are as hereinbefore defined and $R^{17}$ is an alkoxycarbonyl or aldehyde group, with potassium or sodium hydroxide in $C_{1-4}$ alkanol followed by addition of guanidine;

(iii) the reaction of a compound of the formula (VIII):

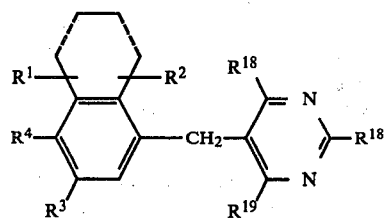

wherein $R^{18}$ is an amino group or a leaving group, such as a $C_{1-4}$ alkylthio group or a halogen atom, $R^{19}$ is a hydrogen or halogen atom, except that both groups $R^{18}$ cannot be amino groups and $R^1$ to $R^4$ and the dotted lines are as hereinbefore defined with an aminating agent such as ammonia and thereafter when $R^{19}$ is a halogen atom removing this by hydrogenolysis;

(iv) the reaction of a compound of the formula (IX):

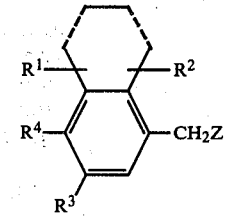

wherein Z is a halogen atom and $R^1$ to $R_4$ and the dotted lines are as hereinbefore defined or Z is hydroxy or di-$C_{1-4}$ alkyl substituted amino, $R^4$ is hydroxy, amino, or mono- or di-$C_{1-4}$ alkyl substituted amino and $R^3$, $R^1$ and $R^2$ are as hereinbefore defined, with a compound of formula (X):

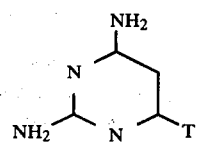

wherein T is a hydroxy or $C_{1-4}$ alkylthio group, and then converting the group T to hydrogen by hydrogenolysis when T is a $C_{1-4}$ alkylthio group or, when T is a hydroxy group, by first converting it to the mesylate or tosylate derivative or to thio, alkylthio or halogen and then removing this by hydrogenolysis;

(b) when it is required to prepare a compound of the formula (II) wherein the 4-position of the phenyl ring is substituted by hydroxy, amino or substituted amino the reaction of a compound of the formula (XI):

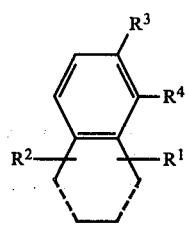

wherein $R^4$ is hydroxy, amino, substituted amino and $R^1$ and $R^3$ and the dotted lines are as hereinbefore defined, with 2,4-diamino-5-hydroxymethylpyrimidine;

(c) the conversion of one compound of the formula (II) to a different compound of the formula (II), for example by the conversion of a hydroxy group to a $C_{1-4}$ alkylthio group or an optionally substituted $C_{1-4}$ alkoxy group or conversion of an amino group to a $C_{1-4}$ alkylthio group or hydrogen, halogen, hydroxy or cyano via a diazo group or to a substituted amino group by methods well known to those skilled in the art.

The reaction of guanidine with a compound of the formula (V) or (VI) will take place under conditions analogous to those described in U.K. Pat. Nos. 1 133 766 and 1 261 455 respectively for the preparation of structurally related benzylpyrimidines. Conveniently the reaction is carried out in a $C_{1-4}$ alkanol, for example methanol or ethanol. The compounds of the formula (V) and (VI) may be prepared by methods known in the art.

The reaction of a compound of the formula (VII) with guanidine and the preparation of the compounds of the formula (VII) will be carried out by methods analogous to those described in Belgian Patent No. 855 505.

In the compounds of the formula (VIII) when $R^{18}$ or $R^{19}$ are halogen atoms these are suitably chlorine or bromine atoms. The reaction may conveniently be carried out under the reaction conditions described in U.K. Pat. Nos. 875 562 and 1 132 082. The reduction of $R^{19}$ when this is halogen will suitably be carried out under the conditions described in German Offenlegungschrift 2258238. This is not a preferred method for preparing those compounds wherein $R^3$ or $R^4$ are groups that are susceptible to catalytic hydrogenation.

The compounds of formula (VIII) may be prepared by methods known in the art, for example as described in U.K. Pat. Nos. 875562 and 1132082 or German Offenlegungschrift No. 2258238. The compounds of the formula (VIII) wherein $R^{18}$ and/or $R^{19}$ are halogen atoms may conveniently be prepared from the corresponding compounds wherein $R^{18}$ and/or $R^{19}$ are hydroxy. These compounds may be prepared by methods analogous to these described in the art or by the reaction of a compound of the formula (XI) with 5-dimethylaminomethyluracil. This reaction will normally be carried out in an inert high boiling polar solvent, for example a high boiling $C_{2-6}$ alkanol such as ethylene glycol, at between 100° and 200° C. for example between 130° and 160° C. The reaction will normally be carried out under basic conditions when the 4-position of the phenyl ring is substituted by hydroxy, for example in the presence of sodium methoxide, and under neutral conditions when the 4-position of the phenyl ring is substituted by amino or substituted amino. Compounds of the formula (VIII) wherein $R^4$ is a hydroxy group may be converted to compounds of the formula (VIII) wherein $R^4$ is an alkoxy or $C_{1-4}$ alkylthio group and compounds of the formula (VIII) wherein $R^4$ is an amino group may be converted to compounds of the formula (VIII) wherein $R^4$ is a $C_{1-4}$ alkylthio or substituted amino group or hydrogen by methods well known to those skilled in the art.

Suitably Z is a dialkylamino or cyclic amino group containing up to 10 carbon atoms; a dimethylamino group is particularly convenient. The reaction will be carried out under conditions well known to those skilled in the art of Mannich reactions. It has been found that the reaction may suitably be carried out at an elevated temperature, suitably between 100° and 200° C. in a solvent having a suitably high boiling point, for example a glycol such as ethylene glycol. The dethiation is suitably carried out by hydrogenolysis in the presence of a transition metal catalyst; Raney nickel is particularly suitable for this purpose. This reaction will normally be carried out in a polar solvent, for example a $C_{1-4}$ alkanol such as methanol or ethanol.

Again, this is not a preferred method of preparing those compounds of the formula (II) wherein there are groups that are susceptible to a catalytic hydrogenation.

The reaction of a compound of the formula (XI) with 2,4-diamino-5-hydroxymethyl pyrimidine will normally be carried out under the reaction conditions described in U.K. Pat. No. 1413471. Thus the reaction will conveniently be carried out in a polar non-phenolic solvent capable of dissolving both reactants at a non-extreme temperature, for example between 50° C. and 150° C. The reaction is preferably carried out in the presence of a strong acid catalyst, such as hydrochloric, acetic, methane sulphonic or toluene-p-sulphonic acids.

It will be apparent to those skilled in the art that when certain ring substituents ($R^3$ and $R^4$) are present in the final compounds of the formula (II) certain methods of preparation will preferably not be used to make these compounds due to the possibility of the reaction conditions changing the final product group.

The intermediates of the formula (V) to (VIII) are novel and as such form a further aspect of the present invention.

In yet another aspect, the present invention provides the first use of the compounds of the formula (II) in human and veterinary medicine. The preferred human use of the compounds of the formula (II) is in the treatment of prophylaxis of bacterial infections.

The following examples illustrate the preparation of the compounds of the present invention and their pharmacological properties. All temperatures are in degrees centigrade.

Pharmacological data

The compounds of the present invention were subjected to standard tests in order to determine the minimum inhibitory concentration in $\mu g/ml$ needed to inhibit a range of bacterial microorganisms in-vitro.

| Compound | |
|---|---|
| TMP | 2,4-Diamino-5-(3,4,5-trimethoxybenzyl)-pyrimidine |
| 1 | 2,4-Diamino-5-(4-methoxy-1-naphthylmethyl)-pyrimidine hydrochloride |
| 2 | 2,4-Diamino-5-(4-amino-3,6-dimethoxy-1-naphthylmethyl)pyrimidine |
| 3 | 2,4-Diamino-5-(4-hydroxy-3-methoxy-1-napthylmethyl)pyrimidine |
| 4 | 2,4-Diamino-5-(3,4-dimethoxy-1-naphthylmethyl)-pyrimidine |
| 5 | 2,4-Diamino-5-(α-naphthylmethyl)pyrimidine |
| 6 | 2,4-Diamino-5-(4-amino-3-methoxy-1-naphthylmethyl)pyrimidine |

EXAMPLE 1

A. 3-Anilino-2-(4-methoxy-1-naphthylmethyl)acrylonitrile

To a solution of 4-methoxy-1-naphthaldehyde (10.0 g, 53.7 mmol) and 3-anilinopropionitrile (9.0 g, 61.6 mmol) in dimethylsulfoxide (25 mL) was added a solution of sodium methoxide (2.9 g, 53.6 mmol) in methanol (25 mL). The resulting mixture was heated to 133° with distillation of the methanol over 45 min. The reaction was then cooled, diluted with ethanol:water and the precipitate that formed was collected, washed with water, ethanol and hexane to give the title compound (10.28 g, 61%); mp 188°–189° after recrystallization from 2-methoxyethanol. Anal. Calcd for $C_{21}H_{18}N_2O$: C, 80.23; H, 5.77; N, 8.91. Found: C, 79.80; H, 5.74; N, 8.87.

B. 2,4-Diamino-5-(4-methoxy-1-naphthylmethyl)-pyrimidine hydrochloride

To 65 mL of ethanolic guanidine solution prepared from 3.42 g (35.8 mmol) of guanidine hydrochloride and 2.00 g (37.0 mmol) of sodium methoxide was added 9.00 g (28.6 mmol) of 3-anilino-2-(4-methoxy-1-naphthylmethyl)acrylonitrile. The solution was heated under reflux for 1.5 hr, and then 60 mL of 2-methoxyethanol was added. The internal temperature was allowed to gradually increase to 108° by distillation of the ethanol, after which it was heated at this temperature for 2.5 hr. The hot mixture was filtered, and the precipitate (7.04 g, 87% of crude product) recrystallized from 30% ethanol in the presence of hydrochloric acid, to give the title compound; mp 312°–314° dec. Anal. Calcd for $C_{16}H_{16}N_4O \cdot HCl$: C, 60.66; H, 5.41; N, 17.69; Cl, 11.19. Found: C, 60.67; H, 5.45; N, 17.70; Cl, 11.19.

EXAMPLE 2

A. 2,4-Diamino-5-(4-hydroxy-3-methoxy-1-naphthylmethyl)pyrimidine

The formate of 2-methoxy-1-naphthol (J. E. Oatis, Jr., M. P. Russell, D. R. Knapp and T. Walle, *J. Med. Chem.* 1981, 24, 309) (7.23 g, 30.3 mmol), 2,4-diamino-5-hydroxymethylpyrimidine (4.35 g, 30.3 mmol), concentrated hydrochloric acid (4.2 mL) and glacial acetic acid (60 mL) were refluxed 2 hr. The resulting dark solution was evaporated to dryness and the residue dissolved in water and neutralized with ammonia. The resulting tan precipitate (5.2 g) was recrystallized from aqueous ethanol containing a slight excess of hydrochloric acid to give title compound as tan powder (2.83 g, 28%); mp ca. 290°–300° dec. Anal. Calcd for $C_{16}H_{16}N_4O_2 \cdot HCl$: C, 57.75; H, 5.15; N, 16.84; Cl, 10.65. Found: C, 57.62; N, 5.21; N, 16.79; Cl, 10.61.

B. 2,4-Diamino-5-(3,4-dimethoxy-1-naphthylmethyl)pyrimidine

To a solution of the product of Example 41A (1.37 g, 4.12 mmol) in dimethyl sulfoxide (15 mL) was added potassium-t-butoxide (0.973 g, 8.24 mmol) followed by methyl iodide (620 mg, 4.12 mmol). After 30 min, water (25 mL) was added and the resulting precipitate chromatographed on silica gel eluted with methanol:methylene chloride (1:20). The title compound crystallized from ethanol as white granules (0.60 g, 47%); mp 228°–230°. Anal. Calcd for $C_{17}H_{18}N_4O_2$: C, 65.79; H, 5.85; N, 18.05. Found: C, 65.70; H, 5.90; N, 18.04.

EXAMPLE 3

2,4-Diamino-5-(4-amino-3,6-dimethoxy-1-naphthylmethyl)pyrimidine dihydrochloride A mixture of 1-amino-2,7-dimethoxynaphthalene (2.03 g, 10.00 mmol) [O. Fischer and W. Kern, *J. Prakt. Chem.*, 94, 34(1916)], 2,4-diamino-5-hydroxymethylpyrimidine (1.40 g, 10.0 mmol), glacial acetic acid (20 mL) and concentrated hydrochloric acid (1.4 mL) was refluxed for 2 hr. The cooled reaction mixture was diluted with acetone and the resulting precipitate was collected and dried giving the title compound as a grey solid (3.40 g, 78%). Recrystallization from aqueous ethanol with concentrated HCl gave an analytical sample, mp >210° dec. Anal. Calcd for $C_{17}H_{19}N_5O_2 \cdot 2HCl \cdot 2H_2O$: C, 47.01; H, 5.80; N, 16.12; Cl, 16.32. Found: C, 47.19; H, 5.90; N, 16.05; Cl, 16.37.

EXAMPLE 4

2,4-Diamino-5-(4-amino-3-methoxy-1-naphthylmethyl)-pyrimidine dihydro chloride

2-Methoxy-1-nitronaphthalene (E. Baltazzi, *Compt. rend.* 1950, 230, 2207) (7.00 g, 34.4 mmol) was reduced to 1-amino-2-methoxynaphthalene [10% Pd-C (0.7 g), ethanol (200 mL), $H_2$ (50 psi)] and immediately refluxed with 2,4-diamino-5-hydroxymethylpyrimidine (4.82 g, 34.4 mmol) in glacial acetic acid (60 mL)-concentrated hydrochloric acid (5.7 mL). After 2 hr, the mixture was cooled and white solid (10.2 g) filtered off. Recrystallization from 95% ethanol gave title compound as white solid (8.06 g, 62% from 2-methoxy-1-nitronaphthalene); mp 232°–234° dec. Anal. Calcd for $C_{16}H_{17}N_5O \cdot 2HCl \cdot 0.6H_2O$: C, 50.70; H, 5.37; N, 18.47; Cl, 18.71. Found: C, 50.78; H, 5.37; N, 18.48; Cl, 18.73.

EXAMPLE 5

Biological Data (A) MIC TABLE 1

| Organisms | Minimum Inhibitory Concentrations ($\mu g/ml$) of selected compounds | | |
|---|---|---|---|
| | TMP | 4 | 5 |
| St. faecalis CN478 | 0.1 | 0.05 | 1.0 |
| St. agalactiae CN1143 | 0.5 | 0.5 | 1.0 |
| Staph. aureus CN491 | 0.5 | 0.05 | 3.0 |
| Vibrio cholerae ATCC14035 | 0.5 | 0.05 | 3.0 |
| Esch. coli CN314 | 0.05 | 0.5 | 3.0 |
| Pr. mirabilis S2409 | 5.0 | 10 | 100 |
| Meningococci (average 5 strains) | 18.0 | 1.1 | — |
| Gonococci (average 17 strains) | 37.1 | 2.0 | — |
| B. fragilis (average 3–10 strains) | 4.0 | 0.7 | — |

(B) MIC TABLE 2

| Compound | MIC ($\mu g/ml$) vs Staph. aureus |
|---|---|
| TMP | 0.5 |
| 1 | 1.0 |
| 2 | 0.05 |
| 3 | 0.05 |
| 6 | 0.05 |

EXAMPLE 6

Tablets

| Ingredient | Amount per tablet (mg) | |
|---|---|---|
| | Single Active Ingredient | Combination |
| 2,4-Diamino-5-(3,4-dimethoxy-1-naphthylmethyl)pyrimidine | 100.0 | 80.0 |
| Sulfamethoxazole | — | 400.0 |
| Lactose | 84.0 | 100.0 |
| Potato starch, dried | 14.3 | 18.0 |
| Magnesium stearate | 0.7 | 1.0 |
| Polyvinylpyrrolidone | 1.0 | 1.0 |

The 2,4-diamino-5-(3,4-dimethoxy-1-naphthylmethyl)pyrimidine, lactose and potato starch (and sulfamethoxazole in the combination formulation) are mixed together and then granulated with aqueous polyvinylpyrolidone. The granules are dried, mixed with the magnesium stearate and then compressed to produce tablets weighing 200 mg each (single active ingredient) or 600 mg each (combination).

EXAMPLE 7

Veterinary Formulation

Syringes for intra-mammary injection into cows are prepared from the following ingredients:

| | |
|---|---|
| 2,4-Diamino-5-(3,4-dimethoxy-1-naphthylmethyl)-pyrimidine | 3.75% w/w |
| Sulfadiazine | 7.50% w/w |
| Glycerol monostearate | 9.50% w/w |
| Tween 65 | 0.50% w/w |
| Arachis oil | 78.75% w/w |

The glycerol monostearate, Tween 65 (a polyethylene oxide sorbitan tristearate) and arachis oil are mixed together and melted at 65° C. The active ingredients (2,4-diamino-5-(3,4-dimethoxy-1-naphthylmethyl)-pyrimidine and sulfadiazine) are mixed in and the mixture homogenized using a high speed stirrer. The resulting mixture is cooled to 50° C. and is filled into intra-mammary syringes using a fill weight of 4.0 g±5%. The manufacture and filling operations are carried out under sterile conditions.

I claim:
1. A compound of the formula

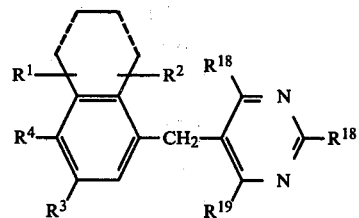

wherein the dotted lines are both single bonds,
$R^{18}$ is amino or $C_{1-4}$ althylthio or halogen,
$R^{19}$ is hydrogen or halogen provided that both $R^{18}$ groups cannot be amino,
$R^1$ and $R^2$ is hydrogen or halogen, $C_{1-4}$ alkyl, $C_{1-4}$ alkylthio, $C_{1-4}$ alkoxy and $R^3$ and $R^4$ are hydrogen, halogen, $C_{2-4}$ alkenyl, $C_{2-4}$ alkenyloxy, nitro, cyano, hydroxy or mercapto except that $R^1$ to $R_4$ may not all be hydrogen and when $R^1$, $R^2$ and $R^3$ are hydrogen, $R^4$ may not be hydroxyl.

* * * * *